(12) United States Patent
Wahab et al.

(10) Patent No.: US 10,744,231 B1
(45) Date of Patent: Aug. 18, 2020

(54) CATHETER COMPRISING PTFE LINER

(71) Applicant: Zeus Industrial Products, Inc., Orangeburg, SC (US)

(72) Inventors: Zahidul Wahab, Orangeburg, SC (US); Guillermo Alpizar, Lexington, SC (US); Patrick Cooper, Orangeburg, SC (US); Jeffrey M. Cox, Manville, NJ (US); Laurence C. Gonzalez, Bridgewater, NJ (US); Daniel Green, Orangeburg, SC (US); Edward Rast, Cameron, SC (US); Bernard Salvador, Bridgewater, NJ (US); Ravinder Singh, Middlesex, NJ (US); Douglas Tourville, Orangeburg, SC (US); Franklin Villagra, Manville, NJ (US)

(73) Assignee: Zeus Industrial Products, Inc., Orangeburg, SC (US)

( * ) Notice: Subject to any disclaimer, the term of this patent is extended or adjusted under 35 U.S.C. 154(b) by 0 days.

(21) Appl. No.: 16/534,020

(22) Filed: Aug. 7, 2019

(51) Int. Cl.
| | |
|---|---|
| *A61M 25/00* | (2006.01) |
| *A61L 29/12* | (2006.01) |
| *A61L 29/14* | (2006.01) |
| *A61L 29/08* | (2006.01) |
| *A61L 29/02* | (2006.01) |

(52) U.S. Cl.
CPC .............. *A61L 29/085* (2013.01); *A61L 29/02* (2013.01); *A61L 29/14* (2013.01); *A61L 2400/10* (2013.01); *A61M 2025/0047* (2013.01); *A61M 2205/0222* (2013.01)

(58) Field of Classification Search
CPC .. A61M 2025/0042; A61M 2025/0047; A61M 2025/0062; A61M 25/0009; A61M 25/0045; A61M 25/005; A61F 2/95; A61B 2017/1205; A61L 29/085; A61L 2400/10; A61L 29/02; A61L 29/14
See application file for complete search history.

(56) References Cited

U.S. PATENT DOCUMENTS

| | | | |
|---|---|---|---|
| 7,341,571 B1 | 3/2008 | Harris et al. | |
| 7,435,466 B2 | 10/2008 | Yoshimoto et al. | |
| 8,377,352 B2 | 2/2013 | Inamoto et al. | |
| 10,183,098 B2 | 1/2019 | Ohshika et al. | |
| 2015/0025562 A1* | 1/2015 | Dinh | A61M 25/0009 606/191 |

OTHER PUBLICATIONS

"Top 5 Reasons to Use Film-Cast PTFE Liner Tubing For Your Next Catheter Design"—2017 Nordson Medical—pp. 1-8.
(Continued)

*Primary Examiner* — Yan Lan
(74) *Attorney, Agent, or Firm* — Louis Isaf; Womble Bond Dickinson (US) LLP (57) ABSTRACT

The present disclosure provides catheters comprising polytetrafluoroethylene (PTFE) tubes with advantageous combinations of strength, flexibility, and size. Such tubes can exhibit features including an average wall thickness of 0.001" or less, a tensile stress at break of greater than 5000 psi, and a storage modulus of less than 100,000 psi at 37° C. These tubes can be also be provided independently (i.e., not within a catheter) and can be employed in various applications.

23 Claims, 8 Drawing Sheets

(56) References Cited

OTHER PUBLICATIONS

"A New Look at PTFE and Thin-Walled Catheter Liners"—Kevin J. Bigham, PhD. Resinate No. 4, Jul. 2017—pp. 1-10.
"New Focus on PTFE"—Kevin J. Bigham, PhD. Resinate Special Edition, Jul. 2018—pp. 1-11.
"Paste Extrusion of Polytetrafluoroethylene Fine Powder Resins" Alfonsius B. Ariawan—The University of British Columbia—Oct. 2001—pp. 1-117.
"Paste Extrusions of Polytetrafluoroethylene (PTFE) Fine Powder Resin: The Effects of Processing Aid Physical Properties" Isaias Ochoa—The University of British Columbia—Apr. 2006—pp. 1-182.
"Processing of Dyneon PTFE Fine Powder" 3M Dyneon PTFE Fie Powder—2015—pp. 1-27.
"Processing Guide Fine Powder PTFE" Inoflon Polytetrafluoroethylene Resins—pp. 1-15.
"Fluoroplastics vol. 1 Non-Melt Processible Fluoroplastics"—The Definitive User's Guid and Databank—PDL Handbook Series—Sina Ebnesajjad—pp. 134-163.

\* cited by examiner

FIGURE 1

| Sample ID | Example 1 | Example 2 | Comparative Example 1 | Comparative Example 2 | Comparative Example 3 | Comparative Example 4 | Comparative Example 5 |
|---|---|---|---|---|---|---|---|
| Sample Type | Extruded liner over wire | Extruded liner over wire | Free extruded liner | Free extruded liner | Dip coated liner | Dip coated liner | Dip coated liner |
| ID | 0.0167 | 0.0705 | 0.0167 | 0.0684 | 0.0717 | 0.0167 | 0.0169 |
| Wall | 0.0005 | 0.00057 | 0.00039 | 0.00052 | 0.00068 | 0.00057 | 0.00067 |
| Tensile Modulus - 1st Segment (psi) (0-5% Tensile Strain) | 43,885 | 65,071 | 292,517 | 242,521 | 68,766 | 51,987 | 42,763 |
| Tensile Modulus - 2nd Segment (psi) (10-50% Tensile Strain) | 11,028 | 4,495 | NA | NA | 1,403 | 1,211 | 679 |
| Tensile Stress at break (psi) | 8516 | 7,748 | 22,077 | 17,362 | 2,475 | 3,949 | 4929 |
| Tensile Stress at 5% elong (psi) | 1267 | 1,573 | 10,699 | 9,756 | 1,810 | 1,504 | 1178 |
| Tesnile Stress at 10% elong (psi) | 1653 | 1,741 | 14,329 | 13,225 | 1,920 | 1,581 | 1236 |
| Tensile Strain at break (%) | 438% | 345% | 312% | 379% | 138% | 314% | 544% |
| Storage Modulus at 23°C (psi) | 90,099 | 58,425 | 371,457 | 291,467 | 68,332 | 99,530 | 81,629 |
| Storage Modulus at 37°C (psi) | 66,152 | 41,192 | 245,217 | 167,501 | 39,760 | 60,828 | 56,596 |
| Storage Modulus decrease/°C | 1,710 | 1,231 | 9,017 | 8,855 | 2,041 | 2,764 | 1,788 |

CATHETER COMPRISING PTFE LINER

FIELD OF THE INVENTION

The present application relates generally to the field of catheters comprising thin wall catheter liners comprising poly(tetrafluoroethylene) (PTFE) and to methods relating to such catheters.

BACKGROUND OF THE INVENTION

Vascular therapy uses minimally invasive, catheter-based procedures and specialized equipment and techniques. Catheters used in these procedures commonly employ a coating or liner on the inner wall to provide a smooth inner surface. A smooth inside diameter (ID) associated with these devices is beneficial in reducing friction against various catheter technologies such as stents, balloons, atherectomy or thrombectomy devices as they are pushed through the tight confines of the catheter lumen. If the catheter ID is not of sufficient lubricity, devices such as stents can cause damage to the liner as the devices are pushed through the catheter lumen. The effect of increased lubricity of the catheter ID is a reduced deployment force of catheter devices as they are passed through the lumen, increasing the likelihood of a successful procedure. The mechanical properties of a catheter liner are also extremely important. For example, high tensile and yield strength may be required when certain devices (e.g., flow diversion tubes, embolization, aneurysm bridging, scaffolding and thrombectomy devices) are passed through catheters in a compressed state. The compressed shape exerts an outward radial force, which causes friction with the ID, commonly making delivery of the device therethrough difficult. On the other hand, high flexibility of a liner is often desirable when catheters must pass through vasculature that involves sharp twist and turns (e.g., cerebral vasculature and below-the-knee (BTK) applications). In this situation, a highly flexible liner with intermediate tensile strength is often more desirable than a high tensile liner with low flexibility/high rigidity.

Various materials have been pursued as inner wall (base liner) materials for use, e.g., within such catheter devices. One material that has been considered is polytetrafluoroethylene (PTFE). PTFE is beneficial as it has a number of beneficial properties, including excellent chemical resistance, high temperature resistance, biocompatibility and very low coefficient of friction/high lubricity.

Known PTFE-based materials for use within catheter applications suffer from various drawbacks. For example, certain extruded PTFE tubes can be produced with sufficiently thin walls and sufficiently high tensile strengths, but exhibit high rigidities and high tensile modulus values, rendering them unsuitable, e.g., in applications where flexibility is important. See, e.g., U.S. Pat. No. 10,183,098 to Ohshika et al. Similarly, modified extruded PTFE tubes have been reported with high tensile strength, but undesirable stiffness, due to the method by which the high tensile strength was obtained. See U.S. Patent Application Publication No. 2015/0025562 to Dinh et al. Dip-coated and film-cast PTFE-based liners have been prepared from PTFE dispersion, and exhibit higher flexibility, but have rather low tensile strengths. Additionally, dip-coating methods are known to be cumbersome and suffer from low productivity (requiring repeated coating/sintering steps). Further, dip-coated tubes typically have relatively low abrasion resistance, as a result of separation of PTFE particles and, as such, the ID of these tubes often have inferior lubricity properties.

It would be beneficial to provide flexible PTFE-based tubes of sufficient strength and methods for preparing such tubes which render the materials suitable, e.g., for use in inner wall (base liner) applications.

SUMMARY OF THE INVENTION

The disclosure provides an extruded polytetrafluoroethylene (PTFE) tube with an average wall thickness less than 0.001 inches, with limited machine direction orientation of PTFE fibrils (resulting in an intermediate tensile strength and low tensile modulus). Due to the very thin walls of the disclosed tubes and the low modulus values of such tubes, they can, in some embodiments, desirably have similar flexibility as dip-coated PTFE liners, but can exhibit better ID lubricity and abrasion resistance than the dip-coated PTFE liners. The combination of properties exhibited by the disclosed tubes, in various embodiments, can render them particularly suitable for use within catheters, including within catheters designed for flexibility, as the thin wall thicknesses and low modulus values of the disclosed tubes provide for a significantly more flexible tube/liner product than traditional thin wall extruded ("free extruded") PTFE liners, as will be described in further detail herein below. It is noted that portions of the specification are described with particular reference to such tubes as catheter liners; however, the tubes and methods disclosed herein are understood to be applicable in other contexts as well, and are not limited to use in catheters.

In one aspect is provided a catheter comprising a passageway surrounded by walls, and further comprising a polytetrafluoroethylene (PTFE) tubular liner within the passageway, the PTFE tube comprising: a) an average wall thickness of 0.001" or less; and b) a tensile stress at break greater than 5000 psi; and c) a storage modulus of less than 100,000 psi at 37° C. In some embodiments, the average wall thickness of the PTFE tubular liner is 0.0002" to 0.0008". In some embodiments, the PTFE tubular liner exhibits a change in the storage modulus between 23° C. and 37° C. of 3,000 psi/° C. or less. In some embodiments, the PTFE tubular liner comprises an abrasion-resistant surface and/or a lubricious surface.

In another aspect is provided a polytetrafluoroethylene (PTFE) tube comprising: an average wall thickness of 0.001" or less; and a tensile stress at break greater than 5000 psi; and a storage modulus of less than 100,000 psi at 37° C. In some embodiments, the average wall thickness is about 0.0002" to about 0.0008". In some embodiments, the tube exhibits a change in the storage modulus between 23° C. and 37° C. of 3,000 psi/° C. or less. In certain embodiments, the tube comprises an abrasion-resistant surface and/or a lubricious surface. Such tubes can, for example, be comprised in a medical device (including, but not limited to, a catheter).

In another aspect is provided a PTFE layer over a metallic core, wherein: the PTFE layer has an average thickness of 0.001" or less; exhibiting an average tensile stress at break greater than 5,000 psi and an average storage modulus of less than 100,000 psi at 37° C. In certain embodiments, the metallic core and PTFE layer are both substantially cylindrical in shape. In some embodiments, the PTFE layer over the metallic core comprises a minimum continuous length of 50 ft. In some embodiments, the PTFE layer exhibits a change in storage modulus between 23° C. and 37° C. of 3,000 psi/° C. or less. The PTFE layer over the metallic core can, in certain embodiments, comprises abrasion resistance and/or comprises a lubricious surface. In preferred embodiments, the values reported for these embodiments are measured by removing the metallic core (such that the reported values relate specifically to the PTFE layer).

In another aspect is provided a polytetrafluoroethylene (PTFE) tube having a characteristic tensile curve with two distinct segments between 0 to 50% elongation with a first segment having an average tensile modulus of 100,000 psi or less and a second segment having a tensile modulus of 25,000 psi or less but greater than 2,500 psi, wherein the PTFE tube has a tensile stress of 3000 psi or less at 5% elongation. In some such embodiments, the tensile stress is 4000 psi or less at 10% elongation.

The present disclosure includes, without limitation, the following embodiments.

Embodiment 1

A catheter comprising a passageway surrounded by walls, and further comprising a polytetrafluoroethylene (PTFE) tubular liner within the passageway, the PTFE tube comprising: a) an average wall thickness of 0.001" or less; and b) a tensile stress at break greater than 5000 psi; and c) a storage modulus of less than 100,000 psi at 37° C.

Embodiment 2

The catheter of the preceding embodiment, wherein the average wall thickness of the PTFE tubular liner is 0.0002" to 0.0008".

Embodiment 3

The catheter of any preceding embodiment, wherein the PTFE tubular liner exhibits a change in the storage modulus between 23° C. and 37° C. of 3,000 psi/° C. or less.

Embodiment 4

The catheter of any preceding embodiment, wherein the PTFE tubular liner comprises an abrasion-resistant surface.

Embodiment 5

The catheter of any preceding embodiment, wherein the PTFE tubular liner comprises a lubricious surface.

Embodiment 6

A polytetrafluoroethylene (PTFE) tube comprising: a) an average wall thickness of 0.001" or less; and b) a tensile stress at break greater than 5000 psi; and c) a storage modulus of less than 100,000 psi at 37° C.

Embodiment 7

A polytetrafluoroethylene (PTFE) tube having a characteristic tensile curve with two distinct segments between 0 to 50% elongation with a first segment having an average tensile modulus of 100,000 psi or less and a second segment having a tensile modulus of 25,000 psi or less but greater than 2,500 psi, wherein the PTFE tube has a tensile stress of 3000 psi or less at 5% elongation.

Embodiment 8

The PTFE tube of any preceding embodiment, wherein the average wall thickness is 0.0002" to 0.0008".

Embodiment 9

The PTFE tube of any preceding embodiment, wherein the tube exhibits a change in the storage modulus between 23° C. and 37° C. of 3,000 psi/° C. or less.

Embodiment 10

The PTFE tube of any preceding embodiment, comprising an abrasion-resistant surface.

Embodiment 11

The PTFE tube of any preceding embodiment, comprising a lubricious surface.

Embodiment 12

The PTFE tube of any preceding embodiment, wherein the tensile strength is 4000 psi or less at 10% elongation.

Embodiment 13

The PTFE tube of any preceding embodiment, comprised in a medical device.

Embodiment 14

The PTFE tube of the preceding embodiment, wherein the medical device is a catheter.

Embodiment 15

A PTFE layer over a metallic core, wherein the PTFE layer has an average thickness of about 0.001" or less, exhibiting an average tensile stress at break greater than 5,000 psi and an average storage modulus of less than 100,000 psi at 37° C.

Embodiment 16

The PTFE layer over the metallic core of the preceding embodiment, wherein the metallic core and PTFE layer are both substantially cylindrical in shape.

Embodiment 17

The PTFE layer over the metallic core of any preceding embodiment, comprising a minimum continuous length of 50 ft.

Embodiment 18

The PTFE layer over the metallic core of any preceding embodiment, wherein the PTFE layer exhibits a change in storage modulus between 23° C. and 37° C. of 3,000 psi/° C. or less.

Embodiment 19

The PTFE layer over the metallic core of any preceding embodiment, comprising abrasion resistance.

Embodiment 20

The PTFE layer over the metallic core of any preceding embodiment, comprising a lubricious surface.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

Figure 1:
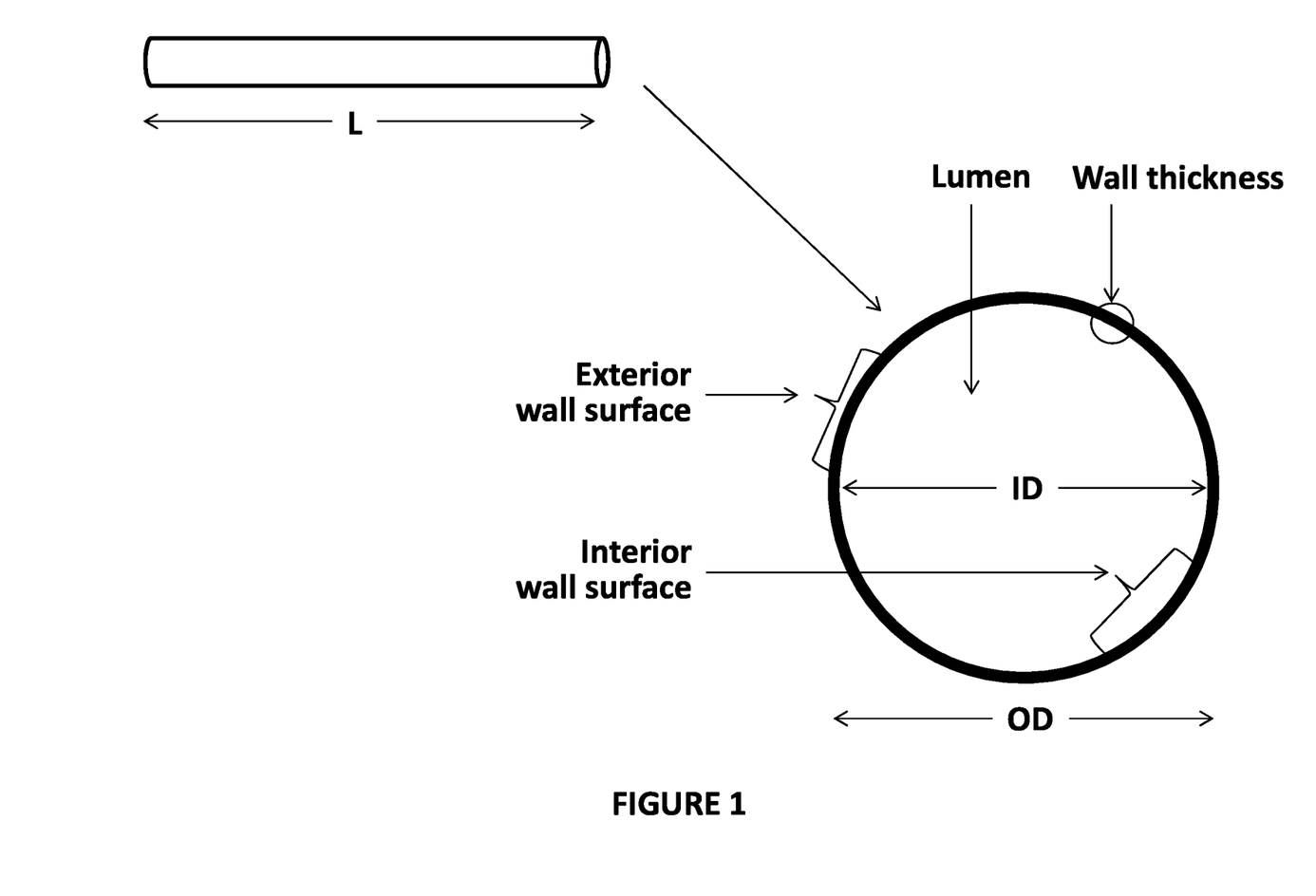
FIG. 1 is a general schematic of a tube of the present disclosure, with relevant parameters, and an expanded schematic of one cross-sectional end face of the tube.

The present disclosure provides an extruded tube comprising polytetrafluoroethylene (PTFE), with certain physical properties as outlined more fully herein below. A general schematic of a tube as provided is shown in FIG. 1. The tube is generally cylindrical in shape. "L" indicates the length of the tube as produced, which can be processed, e.g., cut, to provide tubes of desired length "l" (not shown). The expanded region at the right of FIG. 1 is a cross-sectional view of the interior of the tube. As shown, the "lumen" is an interior region of the tube, i.e., an open channel/cavity (through which, e.g., a catheter device may be passed). The inner diameter of the tube, shown as "ID" is the average distance from a point on the interior wall of the tube to the opposite/farthest point on the interior wall of the tube. The outer diameter of the tube, shown as "OD" is the average distance from a point on the outer wall of the tube through the lumen of the tube to the opposite/farthest point on the outer wall of the tube. As such, the OD value minus the ID value, divided by two provides the average wall thickness of the tube. A representative "wall thickness," "interior wall surface," and "exterior wall surface" of the tube are also shown in FIG. 1.

In certain embodiments, the present disclosure provides extruded PTFE tubes with thin walls. For example, the average thickness of the walls in some embodiments is less than about 0.001". In some embodiments, the average wall thickness of the disclosed tubes can be about 0.0001" to about 0.001", such as about 0.0002" to about 0.001", about 0.0003" to about 0.001", about 0.0004 to about 0.001", or about 0.0005" to about 0.001."

The wall thickness typically does not vary significantly around the circumference of the tube or along the length (L or l) of the tube. As such, the wall thickness can generally be described as substantially uniform. The wall tolerance in some embodiments can be, for example, +/−0.0001" to +/−0.0003" for nominal wall 0.0003" to 0.001" or below. In some embodiments, at any given point on a tube provided according to the present disclosure, the wall thickness is less than about 0.001". In some embodiments, at any given point on a tube provided according to the present disclosure, the wall thickness is about 0.0001" to about 0.001", such as about 0.0002" to about 0.001", about 0.0003" to about 0.001", about 0.0004 to about 0.001", or about 0.0005" to about 0.001." The wall thicknesses may, in some embodiments, be at the lower end of these ranges, e.g., about 0.0001" to about 0.0008", about 0.0002" to about 0.0008", or about 0.0002" to about 0.0006".

The length of the tube can vary widely. An as-produced tube can, in some embodiments, be at least about 50 feet in length. As noted, the length L is not particularly limited, and a tube as schematically shown in FIG. 1 can optionally be processed, e.g., cut into multiple tubes of any desired lengths l. In some embodiments, the length l of a tube provided herein is a length suitable for use in a catheter application, e.g., as a liner. For example, in some embodiments, the length l is about 6" to about 20", such as about 12" to about 20"). Similarly, the ID (which determines the diameter of the lumen) can vary and, in some embodiments, is of a size suitable for use in catheter applications, e.g., as a liner.

The tubes provided herein generally comprise polytetrafluoroethylene (PTFE). Various PTFE resins are commercially available and can be used in certain embodiments to provide the PTFE tubes provided herein. Advantageously in various embodiments, the tubes consist essentially of PTFE, i.e., no additional components (e.g., fillers) are intentionally added to the tubes. The tubes provided herein typically do not comprise any appreciable amount of lubricant (which may, in some embodiments, be used in the method of preparing the tubes, as will be described more fully herein below).

The extruded tubes provided herein generally do not exhibit the high machine direction orientation exhibited by typical PTFE tubes (which are generally stretched to provide the desired strength as a secondary process after production, to enhance the strength thereof). Standard free extruded liners are also strong due to the inherent machine direction orientation imposed by the paste extrusion process used to form them itself. Typically, extruded tubes comprise PTFE fibrils that are at least partially, e.g., substantially, aligned in the machine direction. The tubes provided herein can, in some embodiments, exhibit unique flexibility, rendering them particularly useful, e.g., in applications for which the tube must bend to pass through corners and curves, including, but not limited to, in the context of certain catheter applications. Some of the methods to quantify degree of orientation of polymer molecules include, but are not limited to, X-Ray diffraction, differential scanning calorimetry (DSC), fourier transform infrared (FTIR) spectroscopy, Raman spectroscopy and Birefringence spectroscopy. Tensile testing could also be an indirect method to qualitatively identify the orientation of polymeric materials.

As one example, the degree of fibril orientation may, in some embodiments, be quantified in a PTFE extrudate using Raman spectroscopy. For a material with little to no orientation, Raman spectroscopy generally shows no difference in the scattering intensity at all Raman shifts between two polarization geometries (i.e., parallel or perpendicular to the extrusion direction), indicating no preferred orientation (isotropicity). In the case of an extruded material exhibiting orientation, there is often a difference in the scattering intensity between the two polarization geometries at major Raman shifts. The ratio of Raman scattering intensities at major Raman shifts between two polarization geometries (parallel to perpendicular) may thus, in some embodiments, be used to provide an indication (e.g., a quantitative measure) of the preferred fibril orientation. A ratio of unity indicates isotropicity or no preferred orientation, while a ratio greater than unity indicates a preferred orientation in the direction parallel to the extrusion direction.

The tubes provided herein generally have low rigidity (e.g., at body temperatures of about 37° C.), rendering them suitable for in-vivo use. In some embodiments, the storage modulus is less than 100 ksi at 37° C. In some embodiments, between room temperature (~23° C.) and body temperature (37° C.) the present tube exhibits a storage modulus with low sensitivity to temperature change, remaining at about 3000 psi/° C. (3 ksi/° C.) or less. In some embodiments, the tubes can have flexibilities similar to those exhibited by dip-coated PTFE liners having similar features (e.g., of similar size, wall thickness, etc.).

The tubes described in this disclosure, in some embodiments, have tensile strengths that can be considered moderate. In some embodiments, the PTFE tubes have tensile strengths at break of about 5,000 psi (about 5 ksi) or greater. The tubes, further, in some embodiments, have tensile stress values of about 3,000 psi or less at 5% elongation and tensile strength values of about 4,000 psi or less at 10% elongation. The product also, in certain embodiments, has a characteristic tensile curve with two distinct segments between 0 to 50% elongation with a first segment having an average tensile modulus of 100 ksi or less and a second segment having a tensile modulus of 25 ksi or less but greater than 2,500 psi.

In some embodiments, the PTFE tube has high lubricity and abrasion resistance. Such features can be characterized in varying ways. Abrasion is generally understood to be the wearing down of a material due to friction. The friction is caused by rubbing or scraping the initial material. Abrasion resistance is a material property that prevents wear when friction is applied to the surface. Abrasion resistance is understood to be material-dependent as well as processing-dependent.

There are a variety of methods used to quantify abrasion and wear depending on the sample geometry and the application. In certain embodiments, the material or specimen to be tested is positioned relative to another material such that two surfaces are contacting. The other material can be almost anything as long as it is specified. Some common materials include polished metal surfaces, metal pins, sandpaper, or the same material. Then, one or both materials are moved such that friction is caused between the contacting surfaces. Depending on the test methodology, the end of the test can be defined after a certain amount of time, a defined number of times the surfaces are rubbed, or until a specified failure mode is reached. Some failure modes include reaching: a defined mass loss, a defined reduction of material thickness relative to the initial material thickness, tensile property loss, or insulative property loss. Regardless of the test methodology selected, the relative abrasion resistance of two or more materials can be determined by subjecting the two samples to the same testing conditions and comparing impact of the test conditions on the materials tested. Various methods to evaluate abrasion resistance that can be used to define tubes of the present disclosure include, but are not limited to, those disclosed at www.element.com/materials-testing-services/abrasion-and-wear, www.lectromec.com/test/cable-cable-abrasion, and https://www.en-standard.eu/csn-en-3475-511-aerospace-series-cables-electrical-aircraft-use-test-methods-part-511-cable-to-cable-abrasion/, which are incorporated herein by reference (including, e.g., pin abrasion testing (e.g., using ASTM G132), rubber wheel abrasion testing (e.g., using ASTM G65), taber abrasion testing (e.g., using ASTM D1044 and ASTM D4060), blade-on-block wear testing, medical device wear testing, and pin-on-disk wear testing (e.g., using ASTM G99, ASTM G133, and ASTM F732)). One further exemplary method is EN 3475 Method 511, which generally comprises placing the material (e.g., a wire-coated PTFE as provided herein or a comparative sample) in a fixture so that it is contacting another sample of the same type; the ends are fixed in place and the sample is vibrated/rubbed against itself until there is a current detected between the wires where the insulation has failed.

Tubes provided according to the present disclosure, in various embodiments, exhibit higher abrasion resistance and higher lubricity than commercially available tubes, including dip-coated tubes, which typically have flaking and/or abrasion resistance issues. See, e.g., Examples 3-5, below. Such tubes further, in various embodiments, exhibit higher flexibility than conventional PTFE "free extruded" PTFE liners, e.g., as demonstrated in Examples 1 and 2 (as compared with Comparative Examples 1 and 2 (see, in particular, the tensile modulus and DMA storage modulus data presented therein). Advantageously, such improved properties are exhibited by tubes of the present disclosure particularly for tubes of thin average wall thicknesses, e.g., within the ranges described herein (e.g., less than 0.001"). As such, the tubes are widely applicable, e.g., including for use as PTFE catheter liners.

The disclosure further provides a method for producing PTFE tubes, e.g., tubes exhibiting the physical properties described herein above. The method generally comprises a paste extrusion process, wherein PTFE is extruded over a metallic substrate, e.g., including, but not limited to, a wire. Paste extrusion methods for PTFE are generally known and involve several steps, including: (1) paste preparation or resin mixing with lubricants; (2) preforming; (3) paste extrusion; (4) devolatilization; and (5) sintering, as referenced in further detail below. Fine powder PTFE resins that are suitable for the wire coating paste extrusions disclosed herein are typically non-homopolymer and can be extruded at a reduction ratio of >300. Exemplary resins suitable for this purpose include, but are not limited to, Daikin F205, F201, F201L, F208, and F207 resins, Dyneon TF 2071, TF 2072, and TF 2053 resins, Chemours Teflon 640XT X, 641XT X, CFP 6000 X, 62XT X, 6C X, and 6CN X and Asahi Glass CD 090E, and CD 097E. It is to be understood that the products and methods described herein are not limited to such resins, and any PTFE resins can be reasonably used within the scope of the present disclosure. See, e.g., Fluoroplastics, Vol. 1 (Ebnesajjad, S), Applied Polymer Rheology (Kontopoulou, M), Processing of Dyneon PTFE Fine powder (3M™ Dyneon), Processing Guide: Fine Powder PTFE (INOFLON), Paste Extrusion of Polytetrafluoroethylene fine powder resins (Ariawan, A.B., Ph.D. Dissertation, University of British Columbia), U.S. Pat. No. 10,183,098 to Ohshika et al., and U.S. Pat. No. 8,377,352 to Inamoto et al.), which are incorporated herein by reference in their entireties.

PTFE fine powder can be compacted to a small extent during transportation and storage, even when refrigerated and handled with care, thereby creating lumps. Sifting the cold resin through coarse wire mesh helps break up these lumps. Because the PTFE fine powder is shear, sensitive care must be taken in handling the powder. In some embodiments, in order to extrude PTFE fine powder, it is first uniformly mixed with a lubricant/organic solvent such as Isopar (C, E, G, H, J, K, L, M, N, P, V), Novec (7100, 7200, 7300, 7500, 7700), Naphtha, Shell Sol 340 HT, Shell Sol 142 HT, Mineral spirit 200 HT, methyl nonafluorobutyleether, methylnonafluoro-2-butylether, ethyl nonafluorobutylether, ethylnonafluoro-2-butylether, pentane,1,1,1,2,2,3,4,5,5,5-decafluoro-3-methoxy-4-(trifluoromethyl)-, 2-trifluoromethyl-3-ethoxydodecofluorohexane, furan,2,3,3,4,4-pentafluorotetrahydro-5-methoxy-2,5-bis[1,2,2,2-tetrafluoro-1-(trifluoromethyl)ethyl]-, perfluorooctane, perfluoro (2-butyltetrahydrofuran), perfluorotributylamine, 1,1,2,2,3,3,4,4,4-nonafluoro-N,N-bis(nonafluorobutyl)butan-1-amine, C5-18, Perfluoro N-Alkyl Morpholines, 3M™ Fluorinert (FC-770, FC-3283, FC-40, FC-43, FC-70, FC-75, FC-77), etc. The exact lubricant employed is not particularly limited in the context of the disclosed method. See, e.g., Fluoroplastics, Vol. 1 (Ebnesajjad, S), Applied Polymer Rheology (Kontopoulou, M), Processing of Dyneon PTFE Fine powder (3M™ Dyneon), Processing Guide: Fine Powder PTFE (INOFLON), Paste Extrusion of Polytetrafluoroethylene fine powder resins (Ariawan, A.B., Ph.D. Dissertation, University of British Columbia), 3M™ Thermal management fluids (3M), U.S. Pat. No. 10,183,098 to Ohshika et al., and U.S. Pat. No. 8,377,352 to Inamoto et al., incorporated herein by reference in their entireties.

The lubricant content is generally (but is not limited to) about 35 to 45% based on the total volume of the mixture. The lubricant content should be as low as possible such that driving it off at the devolatilization step is easy and fast, but not so low that the extrusion pressure is excessively high—which is often an issue with thin wall extrusion of PTFE. Increasing the amount of lubricant in the paste mixture helps to keep the extruder pressure within a reasonable/maximum limit. Wettability/surface tension and viscosity are two properties of lubricant that can have a significant impact on the pressure of PTFE paste extrusion and thus can be modified accordingly. A lubricant that wets PTFE more helps reduce the extruder pressure; similarly, a lubricant that is less viscous can help to reduce the extruder pressure.

Before the extrusion step, it is generally important to remove at least some air (advantageously, as much air as possible) from the PTFE/lubricant paste in order to prevent defects in the extrudate. Therefore, in the preforming step, the mixture is typically pressed into shapes (e.g., cylindrical shapes), which are called preform or billets. These preforms are typically quite weak and can easily break or deform and, as such, should be handled with care. The preform advantageously is loaded in the extruder shortly after production (e.g., immediately) to prevent lubricant evaporation.

In certain embodiments, the cylindrical preform is inserted into the extrusion cylinder/barrel of a paste extruder and then pressed through a die with the help of a ram. Extrusion of tubes and wires generally requires the presence of a mandrel in the barrel, which is attached to the back part. According to the present disclosure, the metallic substrate (e.g., wire) is fed through this mandrel. The material of the metallic substrate (e.g., wire) employed in this paste extrusion process is not particularly limited and, in some embodiments, may be copper (e.g., an annealed copper wire), plated copper (e.g., silver-plated copper wire), nickel, stainless steel, nitinol, etc.

The extruded paste material coats the wire that is guided through the extruder head at the same time. In preferred embodiments, as the extrusion pressure changes during processing, the machine design ensures that ram speed and therefore extrusion speed are kept at constant level.

After the extrusion, the residual lubricant in the insulation/PTFE coating must be removed completely by heating above the boiling point of the lubricant/solvent. This step is performed, for example, by passing the product through (or placing the product within) a devolatilization oven.

After the devolatilization, the product is heated in a sintering oven, which is usually set at a temperature equal or higher than the melting point of PTFE (approximately 345° C.). Depending on the line speed and thickness of the PTFE layer, the oven is generally set at well above this temperature. It is important that the product within the sintering oven is completely free of lubricant. In the sintering oven, the PTFE particles melt and adhere to each other. As the product is cooled (e.g., upon exiting/being removed from the sintering oven), the PTFE goes from a molten state to a solid one.

The cooled, coated wire is then stretched and the PTFE coating is removed from the wire. One method for removal of the PTFE coating involves removal of small sections of PTFE coating at two distal locations of the coated wire, exposing the metallic wire. The two exposed metallic locations can be clamped (e.g., using, an Instron tensile machine) and the wire is then stretched. The degree of stretching targeted during this step is usually, for example, at least about 5%, with a maximum stretching percentage of 30% (or until just before wire breaks or the outer diameter of the coated wire reduces down enough to break the bond between the PTFE and the metallic wire). After the wire is stretched sufficiently, the PTFE coating usually slides off easily, in the form of a tube. The removed coating is advantageously in the form of a free-standing tube (of length L). This tube can optionally be processed, e.g., by cutting the long tube into shorter lengths 1 as desired, e.g., for certain specific applications.

The inventors have found that, by extruding PTFE over a metallic substrate such as a wire, little machine-direction orientation of PTFE fibrils is introduced. This feature is in contrast to, e.g., free extruded tubes, which exhibit high machine-direction orientation). By extruding/sintering PTFE coatings in this way and then removing the coating, tubes exhibiting particularly beneficial combinations of properties (as outlined herein above) can be readily obtained. In particular, the inventors have unexpectedly found that tubes with very low wall thicknesses can be obtained in this manner, which exhibit the strength and flexibility features outlined above, providing a particularly beneficial means for the production of very thin-walled PTFE tubes, e.g., for use in catheter applications.

EXPERIMENTALS

Figure 2:
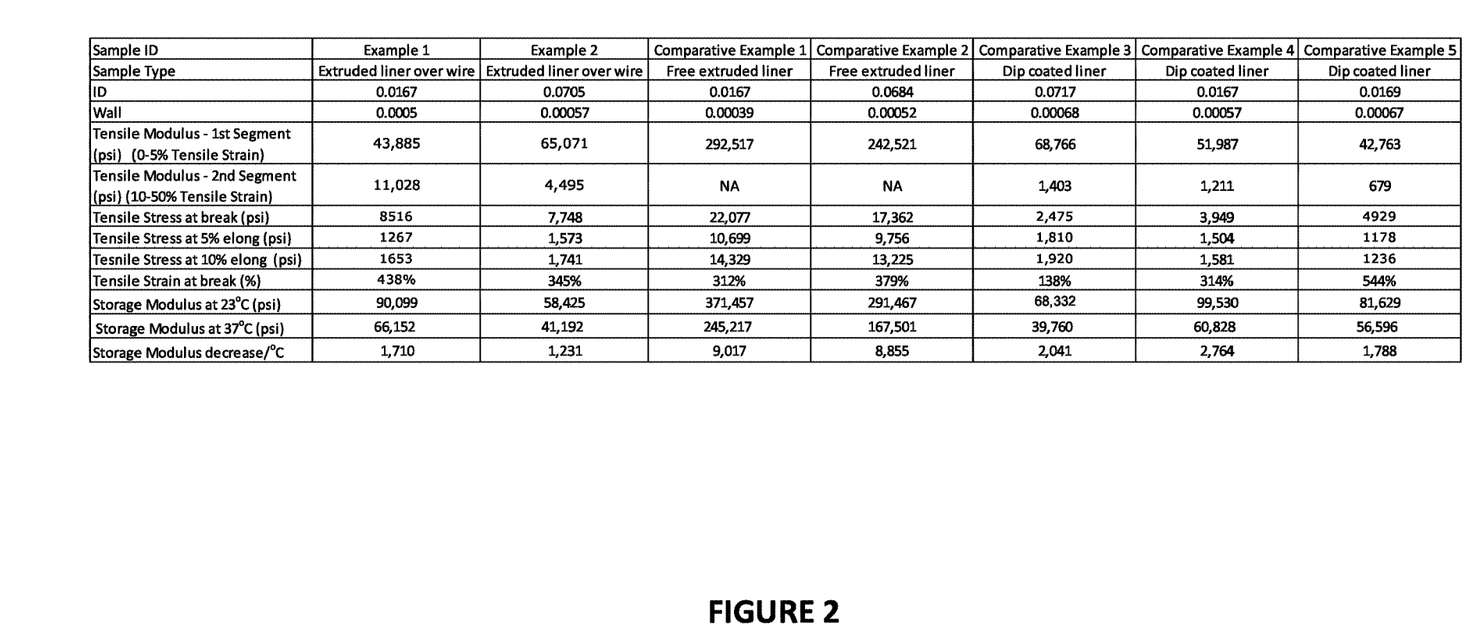
FIG. 2 is a table of various physical parameters associated with certain tubes falling within the scope of the present disclosure, as compared with those associated with comparative tubes.

PTFE Tubes were prepared according to the specific example writeups provided below. An Instron 5965 dual column mechanical tester running Bluehill 3 v3.73.4823 operating software was used to determine the tensile properties of the PTFE tubes. The test was performed at a rate of 2"/min using a 20 lbf load cell attached to pneumatic grips with smooth face inserts set to a 2 inch gage length. At least 5 specimens were tested and the average result is reported in the Table of FIG. 2. During analysis, for tensile modulus determination of the first segment, a straight line was fitted between 0 to 5% elongation/tensile strain. For tensile modulus determination of the second segment, a straight line was fitted between 10 to 50% elongation/tensile strain. Comparative Examples 1 & 2 did not have a second distinct segment. As a result, a straight line could not be fitted properly between 10 to 50% tensile strain and second segment modulus data was not available as a result.

Figure 3:
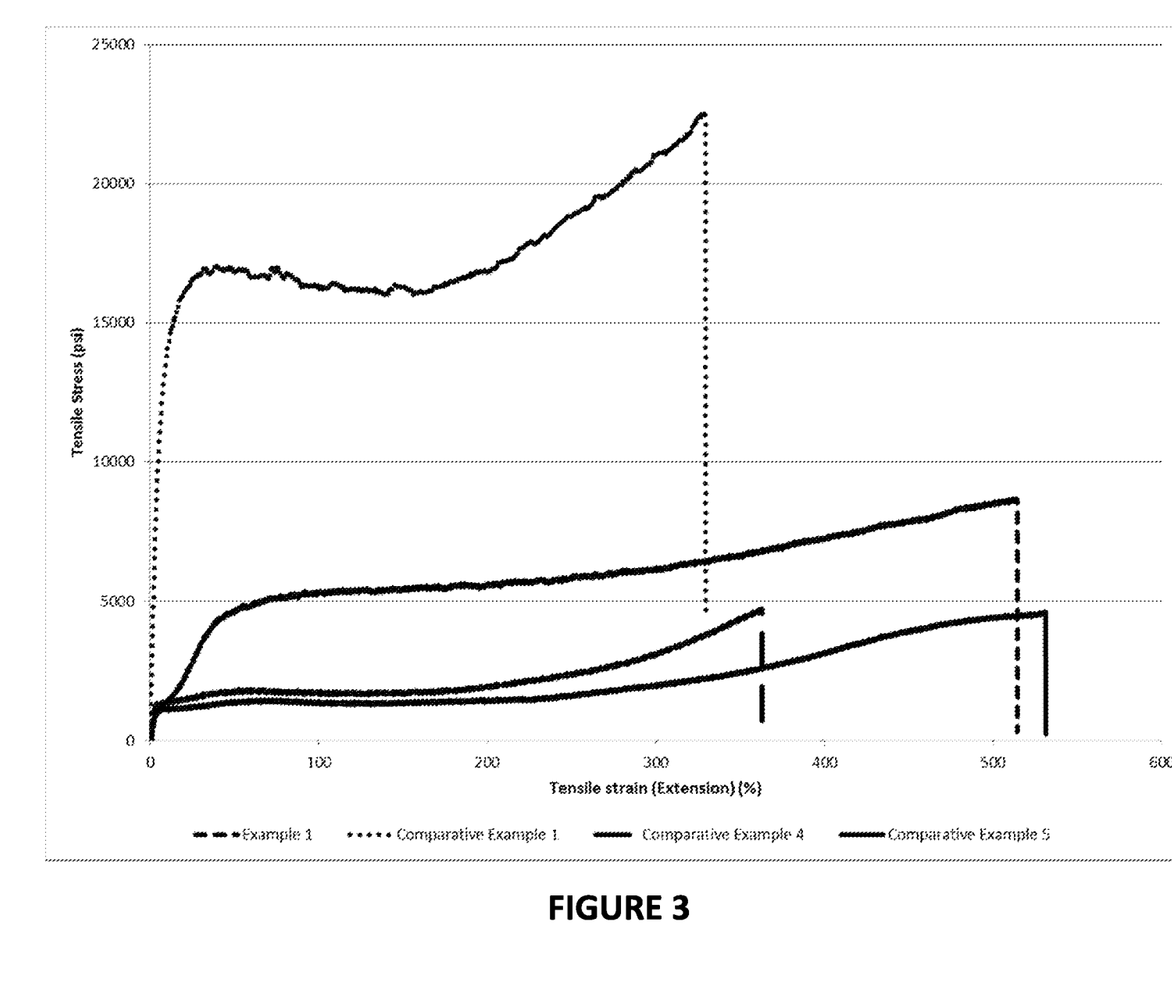
FIG. 3 is a graph of tensile stress v. tensile strain (extension) for a tube of the present disclosure (Example 1) and three comparative examples.
Figure 4:
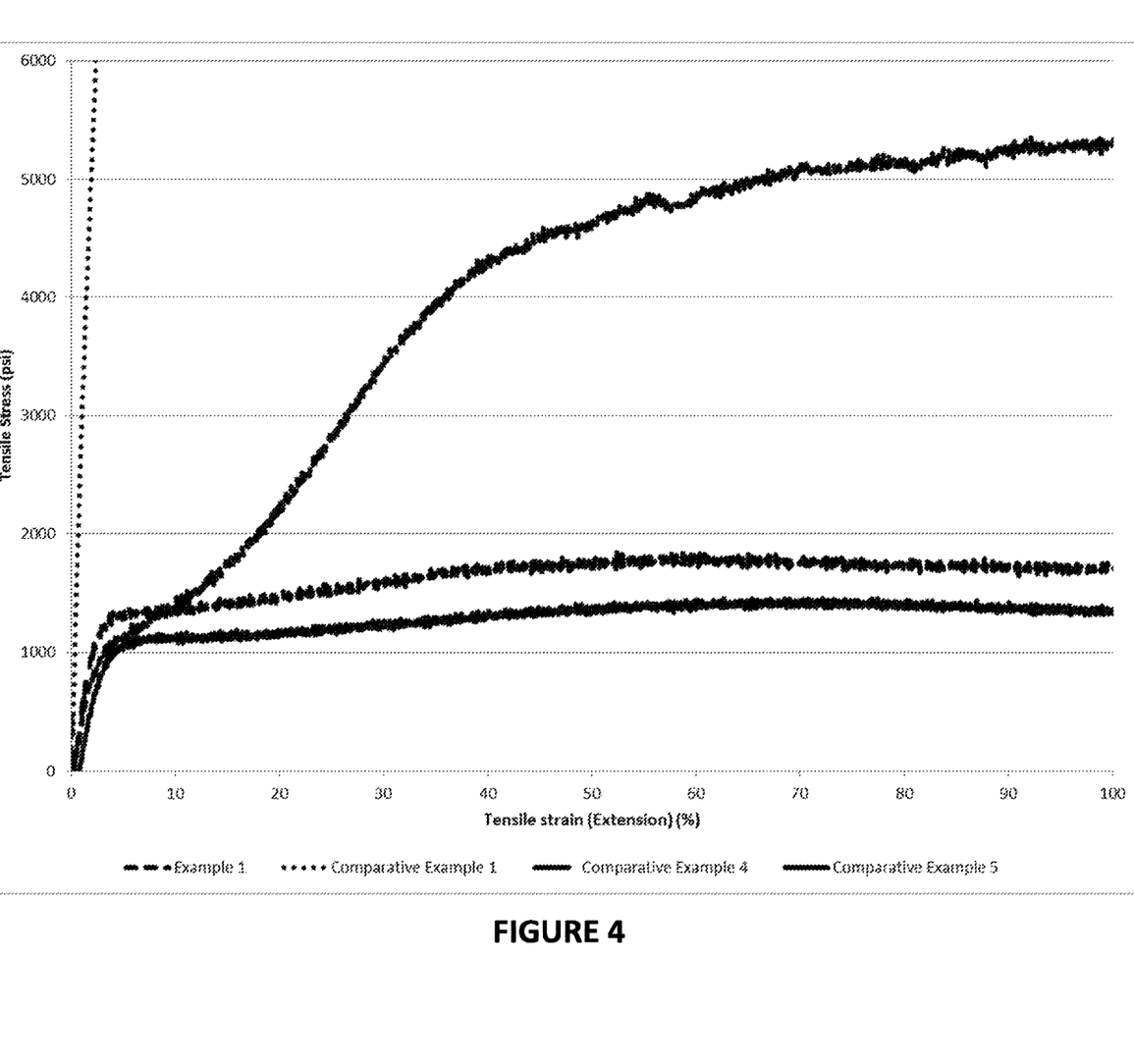
FIG. 4 is an expanded view of a region of the graph of FIG. 3.
Figure 5:
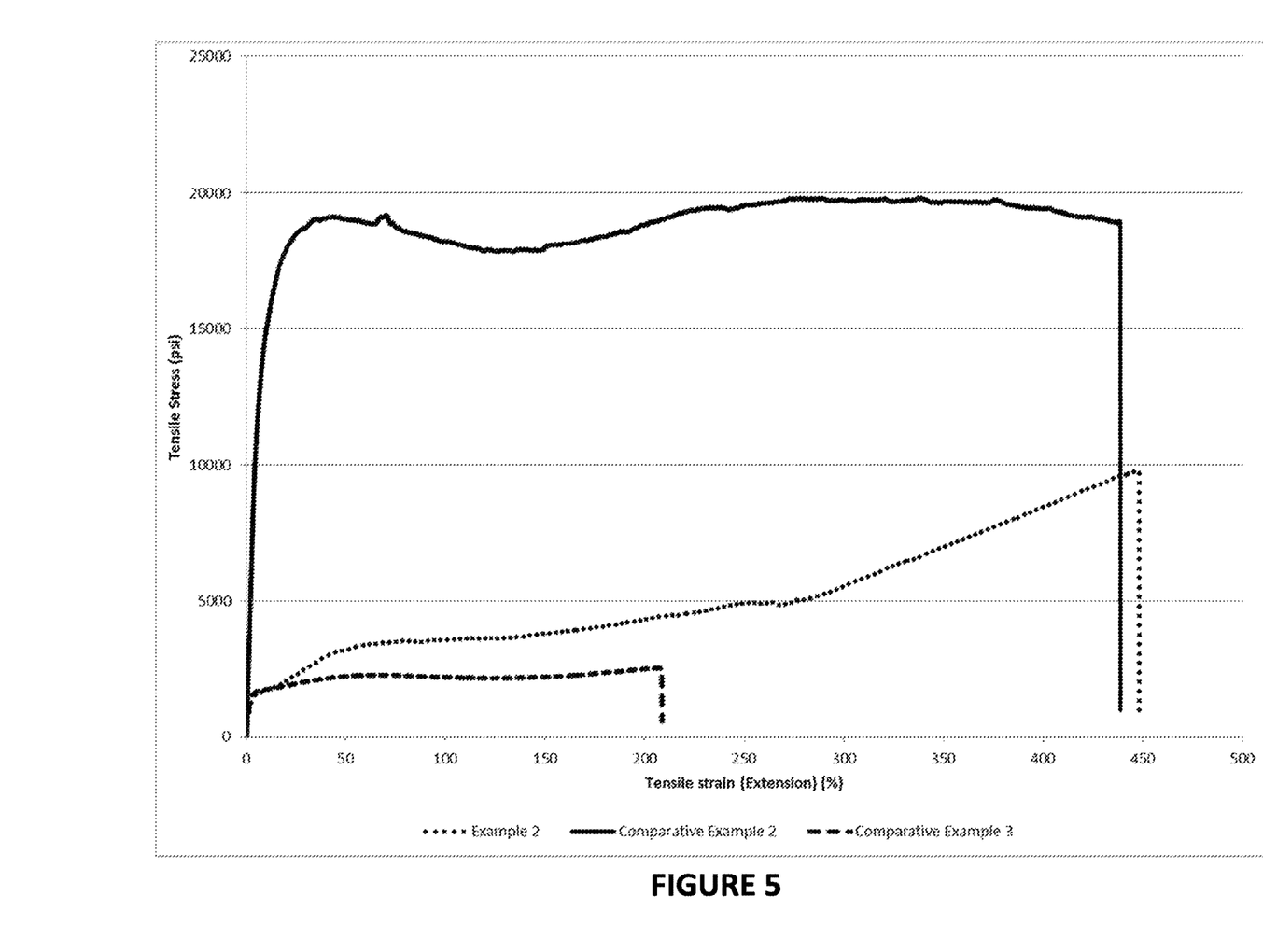
FIG. 5 is a graph of tensile stress v. tensile strain (extension) for a tube of the present disclosure (Example 2) and two comparative examples.
Figure 6:
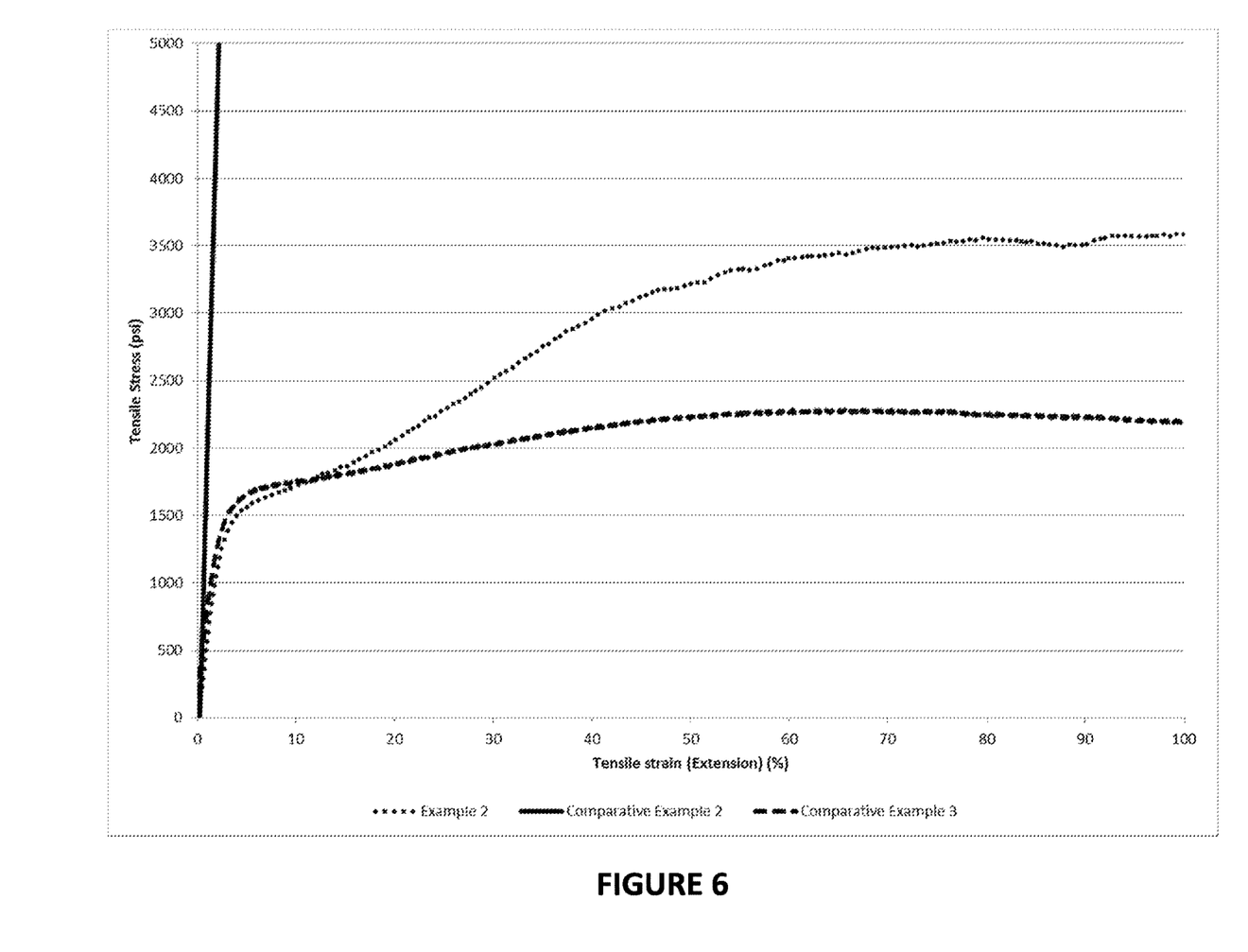
FIG. 6 is an expanded view of a region of the graph of FIG. 5.
Figure 7:
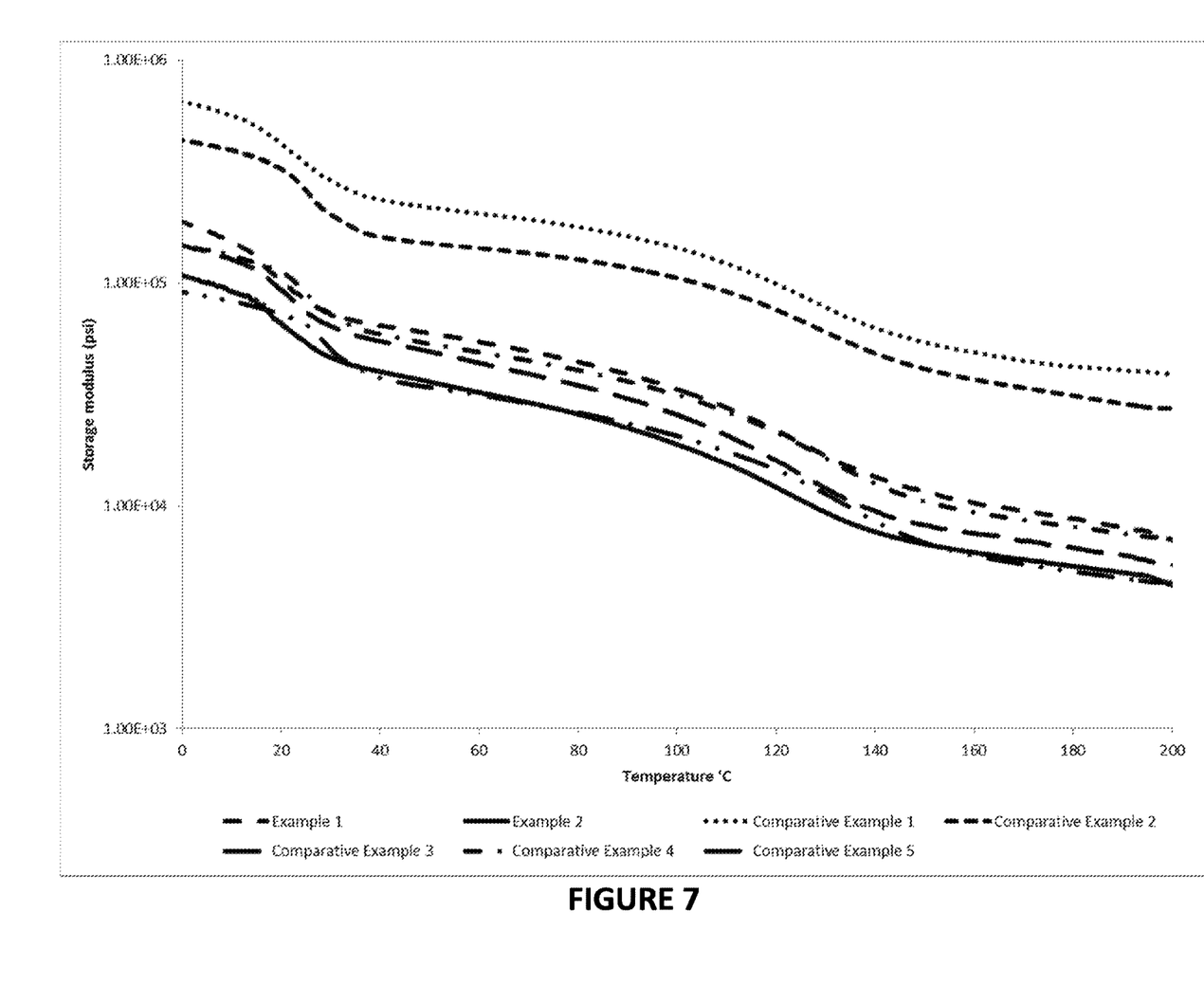
FIG. 7 is a graph of storage modulus v. temperature for tubes of the present disclosure (Examples 1 and 2) and comparative examples.
Figure 8:
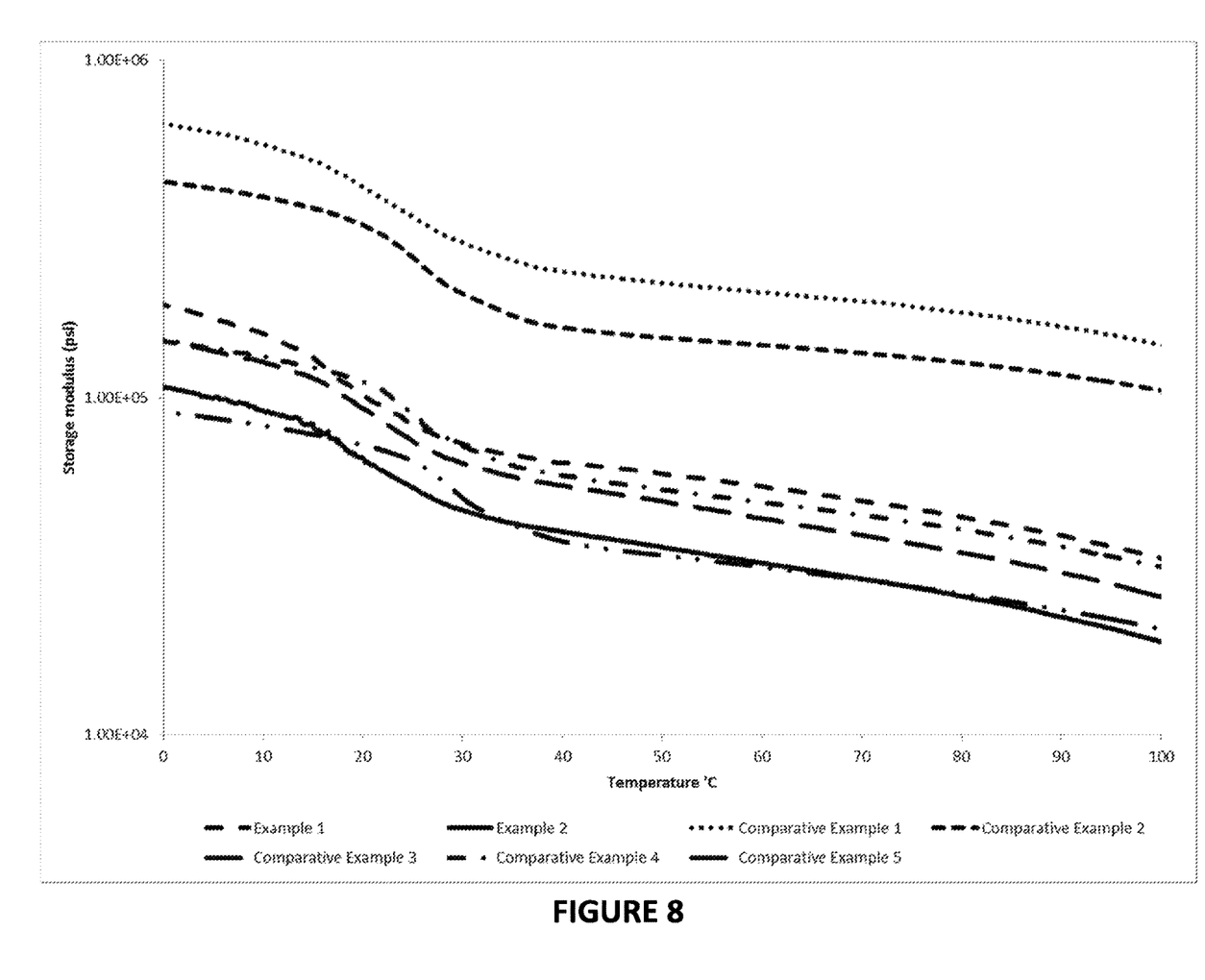
FIG. 8 is an expanded view of a region of the graph of FIG. 7

A TA instruments Q800 DMA with the film tension fixture was used to determine the thermo-mechanical properties of the PTFE tube isolated from the metallic core. The main property of interest was storage modulus (E'). A temperature scan was performed from −100° C. to 300° C. with an isothermal hold for five minutes at −100° C. The sample was heated at a constant rate of 3° C./min while being displaced at a constant amplitude of 15 μm with a fixed frequency tensile oscillation of 1 Hz. The resulting DMA data was imported into TA instruments TRIOS software v4.3. Data comparing the properties of Example 1 against Comparative Examples 1, 4, and 5 (see below) are provided in FIGS. 3 and 4. Data comparing the properties of Example 2 against Comparative Examples 2 and 3 (see below) are provided in FIGS. 5 and 6. Storage modulus properties of all tubes produced (including Examples 1 and 2 and all comparative examples) are provided in FIGS. 7 and 8.

Example 1

A PTFE paste extrusion process was employed (using a medium to high reduction ratio lower MW resin grade) to extrude a 0.0005" thick PTFE layer over an annealed copper wire of 0.0169" OD, followed by devolatilazation of lubricant and sintering of PTFE over the wire. The PTFE layer thickness was determined as follows. The outer diameter (OD) of the coated wire was measured with a laser. The PTFE coating was removed at one location without stretching the wire. The OD of the exposed wire was then measured by laser. Based on these OD readings, the wall thickness of the PTFE tube was calculated. It was ensured that no air gaps are present between the wire and the PTFE layer and coating was smooth and bonded well with the wire. The annealed coated wire was then stretched as described above and the PTFE coating (in tubular form) was removed from the wire without deforming or damaging the PTFE layer to give a free-standing PTFE product in tubular form. This sample was then cut to appropriate length, e.g., for tensile and DMA testing. See FIGS. 3 and 4.

Example 2

The process described in Example 1 was also employed to produce a PTFE tube, with the only exception being that the metallic core used was an annealed copper wire with outer diameter/OD of 0.071". Tensile and DMA tests were also performed on this sample. See FIGS. 5 and 6.

Comparative Example 1

A PTFE paste extrusion process was used to produce a thin wall PTFE tube ("free-extruded tube") with ID of 0.0167" and wall thickness of 0.00057", based generally on the process of Examples 1 and 2, with the exception that no wire substrate was employed. Tensile and DMA tests were also performed on this sample.

Comparative Example 2

The PTFE paste extrusion process referenced in Comparative Example 1 was used to produce a thin wall PTFE tube with ID of 0.0684" and wall thickness of 0.00052". Tensile and DMA tests were also performed on this sample.

Comparative Example 3

A PTFE dip coating/cast film process was used to coat a PTFE layer over an annealed copper wire with 0.071" external diameter. The PTFE layer thickness was 0.00068," determined as follows. The outer diameter (OD) of the coated wire was measured with a laser. The PTFE coating was removed at one location without stretching the wire. The OD was then again measured by laser. Based on these OD readings, the wall thickness of the PTFE tube was calculated. It was ensured that no air gaps are present between the wire and the PTFE layer and coating was smooth and bonded well with the wire. The annealed wire was then stretched and removed without deforming or damaging the PTFE layer. The PTFE product achieved this way was in tubular form. This sample was then cut to appropriate length for tensile and DMA testing.

Comparative Example 4

The same process as used for Comparative Example 3 was used to coat a PTFE layer over an annealed copper wire with external diameter of 0.0169". The PTFE layer thickness was 0.00057". The annealed wire was then stretched and removed without deforming or damaging the PTFE layer, to give a PTFE product in tubular form. This sample was then cut to appropriate length for tensile and DMA testing.

Comparative Example 5

This was a competitive sample and was sourced from an outside vendor, comprising a PTFE layer over an annealed copper wire with 0.0169" external diameter with PTFE layer thickness of 0.00067". The annealed wire was stretched and removed without deforming or damaging the PTFE layer. The PTFE product achieved this way was in tubular form. This sample was then cut to appropriate length for tensile and DMA testing.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A catheter comprising a passageway surrounded by walls, and further comprising a polytetrafluoroethylene (PTFE) tubular liner within the passageway, the PTFE tubular liner comprising:
   a. an average wall thickness of 0.001 inch or less; and
   b. a tensile stress at break greater than 5000 psi; and
   c. a storage modulus of less than 100,000 psi at 23° C.

2. The catheter of claim 1, wherein the average wall thickness of the PTFE tubular liner is 0.0002 inch to 0.0008 inch.

3. The catheter of claim 1, wherein the PTFE tubular liner exhibits a change in the storage modulus between 23° C. and 37° C. of 3,000 psi/° C. or less.

4. The catheter of claim 1, wherein the PTFE tubular liner comprises an abrasion-resistant surface.

5. The catheter of claim 1, wherein the PTFE tubular liner comprises a lubricious surface.

6. A polytetrafluoroethylene (PTFE) tube comprising:
   a. an average wall thickness of 0.001 inch or less; and
   b. a tensile stress at break greater than 5000 psi; and
   c. a storage modulus of less than 100,000 psi at 23° C.

7. The PTFE tube of claim 6, wherein the average wall thickness is 0.0002 inch to 0.0008 inch.

8. The PTFE tube of claim 6, wherein the tube exhibits a change in the storage modulus between 23° C. and 37° C. of 3,000 psi/° C. or less.

9. The PTFE tube of claim 6, comprising an abrasion-resistant surface.

10. The PTFE tube of claim 6, comprising a lubricious surface.

11. The PTFE tube of claim 6 comprised in a medical device.

12. The PTFE tube of claim 11, wherein the medical device is a catheter.

13. The PTFE tube of claim 6, having a characteristic tensile curve with two distinct segments between 0 to 50% elongation with a first segment having an average tensile modulus of 100,000 psi or less and a second segment having a tensile modulus of 25,000 psi or less but greater than 2,500 psi, wherein the PTFE tube has a tensile stress of 3000 psi or less at 5% elongation.

14. A polytetrafluoroethylene (PTFE) tube having a characteristic tensile curve with two distinct segments between 0 to 50% elongation with a first segment having an average tensile modulus of 100,000 psi or less and a second segment having a tensile modulus of 25,000 psi or less but greater than 2,500 psi, wherein the PTFE tube has a tensile stress of 3000 psi or less at 5% elongation.

15. The PTFE tube of claim 14, wherein the tensile strength is 4000 psi or less at 10% elongation.

16. A PTFE layer over a metallic core, wherein the PTFE layer has an average thickness of about 0.001 inch or less, exhibiting an average tensile stress at break greater than 5,000 psi and an average storage modulus of less than 100,000 psi at 23° C.

17. The PTFE layer over the metallic core of claim 16, wherein the metallic core and PTFE layer are both substantially cylindrical in shape.

18. The PTFE layer over the metallic core of claim 16, comprising a minimum continuous length of 50 ft.

19. The PTFE layer over the metallic core of claim 16, wherein the PTFE layer exhibits a change in storage modulus between 23° C. and 37° C. of 3,000 psi/° C. or less.

20. The PTFE layer over the metallic core of claim 16, comprising abrasion resistance.

21. The PTFE layer over the metallic core of claim 16, comprising a lubricious surface.

22. The catheter of claim 1, prepared via extrusion without stretching as a secondary process after extrusion.

23. The catheter of claim 1, prepared via paste extrusion over a metallic substrate.

* * * * *